United States Patent
Fankhauser et al.

(10) Patent No.: US 8,871,967 B2
(45) Date of Patent: Oct. 28, 2014

(54) ESTERS AS PERFUMING INGREDIENTS

(75) Inventors: Peter Fankhauser, Geneva (CH); Umberto Maddalena, Geneva (CH)

(73) Assignee: Firmenich SA, Geneva (CH)

( * ) Notice: Subject to any disclaimer, the term of this patent is extended or adjusted under 35 U.S.C. 154(b) by 432 days.

(21) Appl. No.: 13/501,052

(22) PCT Filed: Oct. 15, 2010

(86) PCT No.: PCT/IB2010/054673
§ 371 (c)(1),
(2), (4) Date: Apr. 9, 2012

(87) PCT Pub. No.: WO2011/055251
PCT Pub. Date: May 12, 2011

(65) Prior Publication Data
US 2012/0195844 A1    Aug. 2, 2012

(30) Foreign Application Priority Data
Nov. 4, 2009 (EP) .................................. 09174999

(51) Int. Cl.
| | | |
|---|---|---|
| *C07C 69/74* | (2006.01) | |
| *C07C 69/533* | (2006.01) | |
| *C07C 69/608* | (2006.01) | |
| *C11B 9/00* | (2006.01) | |
| *C07C 69/24* | (2006.01) | |

(52) U.S. Cl.
CPC .......... *C07C 69/533* (2013.01); *C07C 2101/14* (2013.01); *C07C 69/608* (2013.01); *C11B 9/0034* (2013.01); *C11B 9/003* (2013.01); *C07C 69/24* (2013.01); *C07C 2101/04* (2013.01); *C07C 2101/02* (2013.01)
USPC ................. 560/124; 560/123; 512/8; 512/22; 424/65

(58) Field of Classification Search
CPC   C07C 2101/02; C07C 2101/04; C11B 9/003; A61Q 15/00
USPC .................... 560/123, 124; 512/8, 22; 424/65
See application file for complete search history.

(56) References Cited

U.S. PATENT DOCUMENTS

| | | | | |
|---|---|---|---|---|
| 4,008,258 A | * | 2/1977 | Henrick et al. | ............... 554/219 |
| 2004/0023839 A1 | * | 2/2004 | Goeke et al. | .................... 512/26 |

OTHER PUBLICATIONS

International Search and Written Opinion of the International Searching Authority, application No. PCT/2010/054673, dated Jan. 12, 2011.
Henrick et al., "Ovicidal Activity and Its Relation to Chemical Structure for the Two Spotted Spider Mite (*Tetranychus urticae* Koch) in a New Class of Miticides Containing the Cyclopropyl Group," J. Agric. Food Chem., 24 (5): 1023-1029 (1976).
Le Baut et al., "Acides polyéniques. Activités antifongique et bactériostatique de dérivés de l'acide hexadiène-2,4 oïque," Eur. J. Med. Chem.—Chim. Ther., 18(5):441-445 (1983) (English abstract).
Sakauchi et al., "Syntheses and Odor Descriptions of Cyclopropanated Compounds. Analogs of Aliphatic Monoterpene Dienols and Non-branched Alcohols," Chemistry & Biodiversity, 3:544-552 (2006).

* cited by examiner

*Primary Examiner* — Sudhakar Katakam
(74) *Attorney, Agent, or Firm* — Winston & Strawn LLP

(57) ABSTRACT

The present invention relates to some perfuming ingredients which are esters of formula (I) wherein $R^1$ and $R^2$ represent each a hydrogen atom or a methyl or ethyl group; and $R^3$ represents a $C_5$-$C_8$ group of formula satured or unsaturated linear, branched or cyclic group.

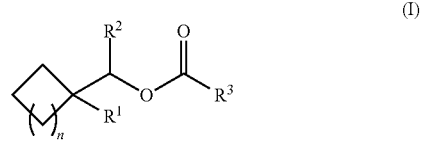

(I)

17 Claims, No Drawings

ESTERS AS PERFUMING INGREDIENTS

This application is a 371 of International Patent Application PCT/IB2010/054673, filed Oct. 15, 2010.

TECHNICAL FIELD

The present invention relates to the field of perfumery. More particularly, it concerns some esters of cyclopropylmethanol or cyclobutylmethanol and their methyl substituted derivatives as defined herein below. The present invention concerns the use of said compounds in the perfumery industry as well as the compositions or articles containing said compounds.

PRIOR ART

To the best of our knowledge, only three compounds of formula (I) are reported in the prior art. Said compounds are cyclopropylmethyl 2,4-hexadienoate, mentioned in *Eur. J. Med. Chem.*, 1983, 18, 441 as a chemical compound in a study for antifungal activity, and cyclopropylmethyl hexanoate and cyclopropylmethyl octanoate, mentioned in *J. Agric. Food Chem.*, 1976, 24, 1023 as a chemical compound in a study for miticides activity.

However, these prior art documents do not report or suggest any organoleptic properties of the compounds of formula (I), or any use of said compounds in the field of perfumery.

One may also cite some analogues of the present invention's compounds which are described as having interesting perfuming properties. These compounds are reported in *Chemistry and Biodiversity*, 2006, pg 544. These documents report three esters of cyclopropylmethanol derivatives (i.e. compounds 9a ([2-ethylcyclopropyl)methyl benzoate], 10a ([2-ethylcyclopropyl)methyl acetate]) and 11a([2-ethylcyclopropyl)methyl butyrate])) which all have a different chemical structure and very different odors (specifically mentioned no green notes). This prior art document does not report or suggest or anticipate any organoleptic properties of the compounds of formula (I), or any use of said compounds in the field of perfumery.

DESCRIPTION OF THE INVENTION

We have now surprisingly discovered that a compound of formula

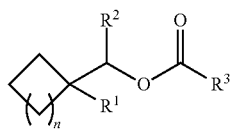

(I)

in the form of any one of its stereoisomers or of a mixture thereof, and wherein n is 0 or 1,
$R^1$ represents a hydrogen atom or a methyl or ethyl group;
$R^2$ represents a hydrogen atom or a methyl or ethyl group; and
$R^3$ represents:
  a) a $C_5$-$C_8$ group of formula

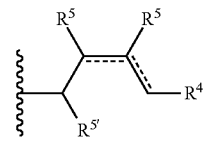

(i)

wherein one dotted line represents a carbon-carbon single or double bond and the other a carbon-carbon single bond;

$R^4$ represents a $C_{1-4}$ alkyl or alkenyl group;
$R^{5'}$ represents a hydrogen atom or a methyl group; and
each $R^5$, taken separately, represents a hydrogen atom or a methyl group, or two $R^5$, taken together, represent a $CH_2$ group (in such a case clearly both dotted lines represent a single bond); or $R^4$ and one $R^5$, taken together, represent a $C_{3-4}$ hydrocarbon group; or
b) a $C_5$-$C_8$ group of formula

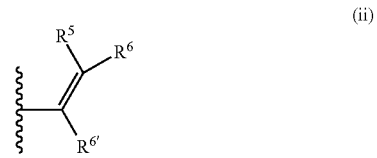

(ii)

wherein $R^6$ represents a $C_{3-4}$ alkyl or alkenyl group, $R^{6'}$ represents a hydrogen atom or a methyl or ethyl group, and $R^5$ is defined as above;

can be used as perfuming ingredient, for instance to impart an odor characterized by a combination of a green note with fruity and/or alliaceous characters or aspects.

For the sake of clarity, by the expression "wherein one dotted line represents a carbon-carbon single or double bond and the other a carbon-carbon single bond", or the similar, it is meant the normal meaning understood by a person skilled in the art, i.e. that the whole bonding (solid and dotted line) between the carbon atoms connected by said dotted line, e.g. carbon 2 and 3, is a carbon-carbon single or double bond.

According to a particular embodiment of the invention, $R^{6'}$ represents a hydrogen atom or a methyl or ethyl group. Alternatively, $R^{6'}$ represents a hydrogen atom.

According to any one of the above embodiments of the invention, $R^1$ and $R^2$ represent each a hydrogen atom or a methyl group. Alternatively, $R^1$ and $R^2$ represent each a hydrogen atom.

According to any one of the above embodiments of the invention, said compounds (I) are those wherein $R^3$ represents:
$a^i$) a $C_5$-$C_7$ group of formula

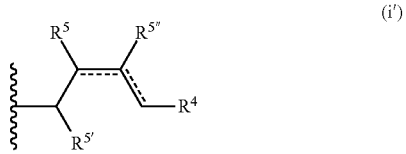

(i')

wherein one dotted line represents a carbon-carbon double bond and the other a carbon-carbon single bond;
$R^4$ represents a $C_{1-3}$ alkyl or alkenyl group, preferably alkyl;
$R^5$ and $R^{5'}$ represent each a hydrogen atom or a methyl group; and
$R^{5''}$, taken alone, represents a hydrogen atom or taken together with $R^5$ represents a $CH_2$ group (in such a case clearly both dotted lines represent a single bond);

a$^{ii}$) a $C_5$-$C_7$ group of formula

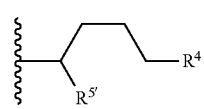

R$^4$ represents a $C_{1-3}$ alkyl or alkenyl group, preferably alkyl;
R$^{5'}$ represents a hydrogen atom or a methyl group;
a$^{iii}$) a $C_6$-$C_8$ group of formula $CH_2(CH_2)_m R^7$, wherein m represents 0 or 1 and R$^7$ represents a $C_{5-6}$ cyclic alkyl or alkenyl group; or
b$^i$) a $C_5$-$C_7$ group of formula

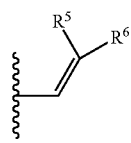

wherein R$^5$ represents a hydrogen atom or a methyl group and R$^6$ represents a $C_3$ alkyl or alkenyl group.

According to a particular embodiment, said invention's compounds are those wherein R$^3$ represents a group as defined under a), said compounds having a green note with a fruity character.

According to a particular embodiment of the invention, said compounds (I) are to those of formula (I) wherein R$^3$ represents a group as defined under a$^i$) or b$^i$).

According to a particular embodiment of the invention, said compounds (I) are those of formula

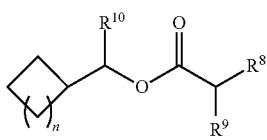

in the form of any one of its stereoisomers or of a mixture thereof, and wherein n is 0 or 1;
R$^{10}$ represents a hydrogen atom or a methyl group;
R$^8$ represents a hydrogen atom or a methyl group; and
R$^9$ represents a $C_{4-6}$ linear alkyl, alkenyl or alkadienyl group or a 2-R$^{11}$-cycloprop-1-yl group, R$^{11}$ representing a methyl, ethyl or propyl group.

According to a particular embodiment of the invention, said compounds (II) are those wherein R$^{10}$ represents a hydrogen atom.

According to a particular embodiment of the invention, said compounds (II) are those wherein n is 0.

According to any one of the above embodiments of said compounds (II), said compounds are those wherein R$^9$ represents a $C_{4-5}$ linear alkyl or alkenyl group or a 2-R$^{11}$-cycloprop-1-yl group, R$^{11}$ representing a methyl or ethyl group.

Alternatively, R$^9$ represents a $C_4$ or $C_5$ linear alkenyl group. Said compounds of formula (II) can be used as perfuming ingredients, for instance to impart an odor characterized by a combination of a green note with fruity and alliaceous aspects.

According to any one of the above embodiments of the invention, said compounds (I) or (II) are $C_{10}$-$C_{13}$ compounds. Alternatively said invention's compounds are $C_{10}$ or $C_{11}$ compounds.

As mentioned above, the compounds of formula (I) possess very interesting odors which allow to distinguish them from other structurally related prior art perfuming ingredients. In particular compounds (I) distinguish themselves by associating a strong green note with a peculiar fruity, e.g. pear, character and often having also a nice alliaceous aspect. Said invention's compounds distinguish them also by lacking a, or by not possessing a significant, woody, citrusy or almond note.

As specific examples of the invention's compounds, one may cite, as non-limiting example, cyclopropylmethyl (3Z)-3-hexenoate which possesses a nice and very strong green note having a clear fruity-pear character, as well as leafy and alliaceous aspects.

This compound distinguishes itself from the other generic green notes, such as the cis-3-hexenol esters, by having a much stronger and performing odor as well as its peculiar fruity-pear character and its unique and natural alliaceous aspect reminding of bear's garlic.

As other example one may cite (E)-cyclopropylmethyl hex-4-enoate, which possesses an odor similar to the one mentioned above but distinguishing itself by having a hexanal note as well as being less powerful than its analogue cyclopropylmethyl (3Z)-3-hexenoate.

As other specific, but non-limiting, examples of the invention's compounds, one may cite the following ones in Table 1.

TABLE 1

Invention's compounds and their odor properties

| Compound structure and name | Odor notes |
|---|---|
| cyclopropylmethyl heptanoate | Green, fruity |
| (E)-cyclopropylmethyl hex-2-enoate | Green, garlic, pepper, slightly fruity |
| cyclopropylmethyl 2-methylhexanoate | Green, fruity and ylang cyclopidene |
| (Z)-1-cyclopropylethyl 3-hexenoate | Green, fruity-pear, alliaceous |

TABLE 1-continued

Invention's compounds and their odor properties

| Compound structure and name | Odor notes |
|---|---|
| (E)-cyclopropylmethyl 3-methylhex-2-enoate | Green, pear, slightly alliaceous, violette |
| cyclopropylmethyl octanoate | Green with fruity aspect |
| cyclopropylmethyl 3-cyclohexylpropanoate | Green, fruity-apple, sweety |
| cyclopropylmethyl hexanoate | Green, sweet fruity, slightly alliaceous, onion |
| (E)-1-cyclopropylethyl 2-methylhex-2-enoate | Green with fruity aspect |
| cyclopropylmethyl 2-(2-ethylcyclopropyl)acetate | Green, fruity |
| cyclopropylmethyl (3E)-3-hexenoate | Green, pear, onion |
| (Z)-cyclobutylmethyl hex-3-enoate | Green, pear, slightly alliaceous |
| mixture of (Z)-cyclopropylmethyl 3-methylhept-2-enoate and (E)-cyclopropylmethyl 3-methylhept-2-enoate | Green, pear |
| (Z)-(1-methylcyclopropyl)methyl hex-3-enoate | Green, pear, pine, alliaceous |

According to a particular embodiment of the invention, the compound of formula (I) is cyclopropylmethyl (3Z)-3-hexenoate, (E)-cyclopropylmethyl hex-4-enoate or (Z)-cyclobutylmethyl hex-3-enoate, (E)-cyclopropylmethyl hex-2-enoate, cyclopropylmethyl 2-methylhexanoate, (Z)-1-cyclopropylethyl 3-hexenoate, cyclopropylmethyl 3-cyclohexylpropanoate, cyclopropylmethyl hexanoate, (E)-1-cyclopropylethyl 2-methylhex-2-enoate, cyclopropylmethyl (3E)-3-hexenoate, (Z)-cyclobutylmethyl hex-3-enoate, (Z)-(1-methylcyclopropyl)methyl hex-3-enoate, (Z)-cyclopropylmethyl 3-methylhept-2-enoate or (E)-cyclopropylmethyl 3-methylhept-2-enoate.

According to a particular embodiment of the invention, the compound of formula (I) is cyclopropylmethyl (3Z)-3-hexenoate, or (E)-cyclopropylmethyl hex-4-enoate or (Z)-cyclobutylmethyl hex-3-enoate.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:

i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualitat, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carriers, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefits such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery, i.e. fine or functional perfumery, to positively impart or modify the odor of a consumer product into which said compound (I) is added. Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, hair, textile, or home surface). In other words, a perfuming consumer product according to the invention comprises the functional formulation, as well as optionally additional benefit agents, corresponding to the desired consumer product, e.g. a detergent or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer bases can be a perfume, such as a fine perfume, a cologne or an after-shave lotion; a fabric care product, such as a liquid or solid detergent, a fabric softener, a fabric refresher, an ironing water, a paper, or a bleach; a body-care product, such as a hair care product (e.g. a shampoo, a coloring preparation or a hair spray), a cosmetic preparation (e.g. a vanishing cream or a deodorant or antiperspirant), or a skin-care product (e.g. a perfumed soap, shower or bath mousse, oil or gel, or a hygiene product); an air care product, such as an air freshener or a "ready to use" powdered air freshener; or a home care product, such as a wipe, a dish detergent or hard-surface detergent.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 3% by weight, or even more, of the compounds of the invention based on the weight of the composition into which they are incorporated. Concentrations lower than these, such as in the order of 0.001% to 2% by weight, can be used when these compounds are incorporated into perfumed articles, percentage being relative to the weight of the article.

The invention's compounds can be prepared according to a method involving a trans esterification of an appropriate ester of the acid $R^3COOH$, e.g. a methyl or ethyl ester of $R^3COOH$, with an appropriate alcohol, such as cyclopropylmethanol. Alternatively the compounds (I) can be obtained by a direct esterification of an acid $R^3COOH$ with an appropriate alcohol. Typical examples are provided herein below in the Examples section.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)
General Procedures for Obtaining the Invention's Compounds
Ester Preparation—Method A The carboxylic acid (69 mmol), the cycloaliphatic alcohol (62 mmol), p-toluenesulphonic acid hydrate (0.16 g; 0.84 mmol) and n-heptane (30 g) were charged in a 100 ml round bottom flask and heated to reflux. The water formed by the reaction was removed using a Dean Stark trap. The reaction progress was monitored by GC. After a few hours, having achieved full conversion, the reaction mixture was cooled to room temperature, diluted with MTBE (30 ml) and washed repeatedly with aq. sodium carbonate. Drying over anh. sodium sulphate, filtration and removal of the solvent afforded the crude ester in quantitative yield.

Distillation through a 15 cm Vigreux column or flash distillation (bulb to bulb) under reduced pressure gave the pure ester.

Ester Preparation—Method B

The methyl carboxylate (116 mmol), the cycloaliphatic alcohol (234 mmol), dioctyl tin oxide (1.0 g; 2.8 mmol) and n-heptane (20 g) were charged in a 100 ml round bottom flask and heated to reflux. The methanol formed by the reaction was removed using a Dean Stark trap. The reaction progress was monitored by GC. After 24 hours the solvent was distilled off to yield the crude ester in quantitative yield. Distillation through a 15 cm Vigreux column under reduced pressure gave the pure ester.

Ester Preparation—Method C

The alkyl carboxylate (364 mmol), the cycloaliphatic alcohol (277 mmol) and dioctyl tin oxide (1.0 g; 2.8 mmol) were charged in the distillation flask of a 35 cm Fischer Spaltrohr® column and heated to 120-130° C. Vacuum was applied, to continuously distill the alkanol formed by transesterification. The reflux ratio and distillation rate were adjusted in order to distill alkanol containing only a minimum amount of the higher-boiling cycloaliphatic alcohol. The reaction progress was monitored by GC. As the reaction rate slowed down another portion of cycloaliphatic alcohol (97 mmol) was added, to increase further the conversion of the starting alkyl carboxylate. Finally the desired ester was distilled under reduced pressure using the same apparatus.

Hydrogenation—General Method

The unsaturated ester (35 mmol), palladium on charcoal (5% Pd/C, 0.3 g) and ethyl acetate (30 ml) were charged in a 100 ml stirred autoclave and hydrogenated (4 bar hydrogen) at 25° C. for 24 hours. Filtration over Celite and removal of the solvent followed by flash distillation (bulb to bulb) under vacuum afforded the desired saturated ester.

Cyclopropanation—General Method

To an oven dried 1000 ml round bottomed flask was added methylene chloride (500 ml) under an argon atmosphere. Diethylzinc (100 ml, 1M in hexanes; 100 mmol) was added, and then diiodomethane (57.0 g, 213 mmol) was introduced dropwise over 1.5 hours. Following stirring for 30 minutes (a white precipitate formed) the unsaturated ester (36 mmol) was added dropwise over 20 minutes and the reaction was stirred over night at room temperature. The reaction mixture was poured into a 20% aq. potassium carbonate solution (500 ml) and then filtered through a pad of Celite in a sintered funnel. The organic layer was separated and dried over anh. sodium sulfate. Filtration of the drying agent, concentration and flash distillation gave the crude cyclopropanated material. This product, containing still some starting ester was subjected to a second cyclopropanation procedure. Distillation through a 15 cm Vigreux column under reduced pressure gave the pure cyclopropanated ester.

Using the above general procedure were prepared the following compounds:

(Z)-cyclopropylmethyl hex-3-enoate

Prepared from (Z)-methyl hex-3-enoate and cyclopropanemethanol according to the ester preparation method B described above. Alternatively prepared from (Z)-n-butyl hex-3-enoate and cyclopropanemethanol according to the ester preparation method C.

Bp.: 103° C./13 mbar $^{13}C$-NMR: 3.2 (t), 9.8 (d), 13.9 (q), 20.8 (t), 32.9 (t), 69.4 (t), 120.4 (d), 135.0 (d), 172.2 (s);

¹H-NMR: 0.26-0.30 (m, 2H); 0.54-0.59 (m, 2H); 0.99 (t, J=7.4, 3H); 1.07-1.18 (m, 1H); 2.03-2.10 (m, 2H); 3.11 (d, J=6.30, 2H); 3.92 (d, J=7.4, 2H); 5.50-5.60 (m, 2H).

(E)-cyclopropylmethyl hex-3-enoate

Prepared from (E)-methyl hex-3-enoate and cyclopropanemethanol according to the ester preparation method B described above.
Bp.: 71° C./4.5 mbar
¹³C-NMR: 3.2 (t), 9.8 (d), 13.5 (q), 25.5 (t), 38.1 (t), 69.3 (t), 120.7 (d), 136.2 (d), 172.4 (s);
¹H-NMR: 0.26-0.30 (m, 2H); 0.54-0.59 (m, 2H); 0.99 (t, J=7.2, 3H); 1.07-1.18 (m, 1H); 2.02-2.09 (m, 2H); 3.04 (d, J=6.30, 2H); 3.91 (d, J=7.4, 2H); 5.50-5.65 (m, 2H).

(E)-cyclopropylmethyl hex-2-enoate

Prepared from (E)-methyl hex-2-enoate and cyclopropanemethanol according to the ester preparation method B described above.
Bp.: 61° C./1 mbar
¹³C-NMR: 3.2 (t), 9.9 (d), 13.7 (q), 21.3 (t), 34.2 (t), 69.0 (t), 121.4 (d), 149.3 (d), 166.9 (s);
¹H-NMR: 0.27-0.31 (m, 2H); 0.55-0.60 (m, 2H); 0.94 (t, J=7.5, 3H); 1.10-1.20 (m, 1H); 1.45-1.54 (m, 2H); 2.16-2.21 (m, 2H); 3.96 (d, J=7.2, 2H); 5.85 (d, J=15.2; H); 6.94-7.02 (m, 1H).

Cyclopropylmethyl 3-methylhex-2-enoate

Prepared from methyl 3-methylhex-2-enoate and cyclopropanemethanol according to the ester preparation method B described above. The Z and E isomer were separated by distillation under vacuum using a 35 cm Fischer Spaltrohr® column.
Z-Isomer:
Bp.: 60° C./2.5 mbar
¹³C-NMR: 3.2 (t), 9.9 (d), 14.1 (q), 21.5 (t), 25.2 (q), 35.3 (t), 68.3 (t), 116.3 (d), 160.5 (s), 166.5 (s);
¹H-NMR: 0.25-0.30 (m, 2H); 0.53-0.58 (m, 2H); 0.95 (t, J=7.5, 3H); 1.09-1.19 (m, 1H); 1.46-1.56 (m, 2H); 1.88 (s, 3H); 2.61 (t, 2H); 3.91 (d, J=7.2, 2H); 5.70 (s, 1H).
E-Isomer:
Bp.: 75° C./2.5 mbar
¹³C-NMR: 3.3 (t), 9.9 (d), 13.7 (q), 18.7 (q), 20.6 (t), 43.0 (t), 68.3 (t), 115.6 (d), 160.1 (s), 167.0 (s);
¹H-NMR: 0.26-0.30 (m, 2H); 0.54-0.59 (m, 2H); 0.92 (t, J=7.5, 3H); 1.09-1.19 (m, 1H); 1.47-1.56 (m, 2H); 2.12 (t, 2H); 2.15 (s, 3H); 3.92 (d, J=7.2 Hz, 2H); 5.7 (s, 1H).

(Z)-1-cyclopropylethyl 3-hexenoate

Prepared from methyl (3Z)-3-hexenoate and cyclopropyl methyl carbinol according to the ester preparation method B described above.
Bp.: 68° C./3.8 mbar
¹³C-NMR: 2.5 (t), 3.5 (t), 13.9 (q), 16.4 (d), 19.8 (q), 20.8 (t), 33.3 (t), 75.3 (d), 120.6 (d), 135.0 (d), 171.6 (s);
¹H-NMR: 0.20-0.26 (m, 1H); 0.35-0.40 (m, 1H); 0.45-0.56 (m, 2H); 0.94-1.03 (m, 1H); 0.98 (t, J=7.5, 3H); 1.29 (d, J=6.4, 3H); 2.03-2.11 (m, 2H); 3.07 (d, J=6.7, 2H); 4.31-4.38 (m, 1H); 5.50-5.61 (m, 2H).

Cyclopropylmethyl Hexanoate

Prepared from hexanoic acid and cyclopropanemethanol according to the ester preparation method A described above.

Bp.: 65° C./6 mbar
¹³C NMR: 3.2 (t), 9.9 (d), 13.9 (q), 22.4 (t), 24.8 (t), 31.4 (t), 34.4 (t), 69.0 (t), 174.0 (s);
¹H-NMR: 0.25-0.29 (m, 2H); 0.53-0.58 (m, 2H); 0.90 (t, J=7.1, 3H); 1.07-1.17 (m, 1H); 1.28-1.36 (m, 4H); 1.61-1.68 (m, 2H); 2.31 (t, J=7.7, 2H); 3.90 (d, J=7.3, 2H).

(E)-cyclopropylmethyl hex-4-enoate

Prepared from (E)-methyl hex-4-enoate and cyclopropanemethanol according to the ester preparation method B described above.
Bp.: 60-65° C./2 mbar
¹³C NMR: 3.2 (t), 9.8 (d), 17.9 (q), 28.0 (t), 34.4 (t), 69.1 (t), 126.1 (d), 129.3 (d), 173.4 (s);
¹H-NMR: 0.25-0.29 (m, 2H); 0.53-0.58 (m, 2H); 1.07-1.17 (m, 1H); 1.64 (d, J=6.0 Hz, 3H); 2.28-2.40 (m, 4H); 3.90 (d, J=7.3, 2H); 5.39-5.53 (m, 2H).

Cyclopropylmethyl Heptanoate

Prepared from allyl heptanoate and cyclopropanemethanol according to the ester preparation method C described above.
Bp.: 71° C./2 mbar
¹³C NMR: 3.2 (t), 9.9 (d), 14.0 (q), 22.5 (t), 25.0 (t), 28.9 (t), 31.5 (t), 34.4 (t), 69.0 (t), 174.0 (s);
¹H-NMR: 0.25-0.29 (m, 2H); 0.53-0.58 (m, 2H); 0.89 (t, J=7.1, 3H); 1.07-1.17 (m, 1H); 1.25-1.37 (m, 6H), 1.60-1.67 (m, 2H); 2.31 (t, J=7.6, 2H); 3.90 (d, J=7.3, 2H).

Cyclopropylmethyl 3-cyclohexylpropanoate

Prepared from allyl 3-cyclohexylpropanoate and cyclopropanemethanol according to the ester preparation method C described above.
Bp.: 66° C./0.1 mbar
¹³C NMR: 3.2 (t), 9.9 (d), 26.3 (t), 26.6 (t), 32.0 (t), 32.4 (t), 33.0 (t), 37.3 (d), 69.0 (t), 174.3 (s);
¹H-NMR: 0.25-0.29 (m, 2H); 0.53-0.58 (m, 2H); 0.84-0.95 (m, 2H); 1.07-1.30 (m, 5H); 1.51-1.57 (m, 2H); 1.62-1.73 (m, 5H); 2.33 (t, J=7.9, 2H); 3.90 (d, J=7.3, 2H).

Cyclopropylmethyl Octanoate

Prepared from allyl octanoate and cyclopropanemethanol according to the ester preparation method C described above.
Bp.: 76° C./0.1 mbar
¹³C-NMR: 3.2 (t), 9.9 (d), 14.1 (q), 22.6 (t), 25.1 (t), 29.0 (t), 29.2 (t), 31.7 (t), 34.4 (t), 69.0 (t), 174.0 (s);
¹H-NMR: 0.25-0.29 (m, 2H); 0.53-0.58 (m, 2H); 0.88 (t, J=7.0, 3H); 1.07-1.17 (m, 1H); 1.25-1.37 (m, 8H), 1.60-1.67 (m, 2H); 2.31 (t, J=7.5, 2H); 3.90 (d, J=7.3, 2H).

Cyclopropylmethyl 2-methylhexanoate

Prepared from 2-methylhexanoic acid and cyclopropanemethanol according to the ester preparation method A described above.
Bp.: 65° C./1 mbar
¹³C-NMR: 3.2 (t), 9.9 (d), 14.0 (q), 17.2 (q), 22.6 (t), 29.5 (t), 33.6 (t), 39.6 (d), 68.8 (t), 177.1 (s);
¹H-NMR: 0.25-0.29 (m, 2H); 0.53-0.58 (m, 2H); 0.89 (t, J=7.0, 3H); 1.07-1.17 (m, 1H); 1.15 (d, J=7.0, 3H); 1.24-1.35 (m, 4H); 1.38-1.47 (m, 1H); 1.62-1.71 (m, 1H); 2.40-2.49 (m, 1H); 3.91 (d, J=7.2, 2H).

(E)-1-cyclopropylethyl 2-methyl-2-hexenoate

Prepared from ethyl (E)-2-methyl-2-hexenoate and cyclopropyl methyl carbinol according to the ester preparation method C described above.

Bp.: 72° C./2 mbar $^{13}$C-NMR: 2.4 (t), 3.5 (t), 12.4 (q), 14.0 (q), 16.4 (d), 19.9 (q), 21.9 (t), 30.8 (t), 74.8 (d), 128.3 (s), 141.9 (d), 167.9 (s);

$^{1}$H-NMR: 0.22-0.28 (m, 1H); 0.37-0.43 (m, 1H); 0.46-0.56 (m, 2H); 0.95 (t, J=7.5, 3H); 0.98-1.06 (m, 1H); 1.32 (d, J=6.3, 3H); 1.44-1.53 (m, 2H); 1.83 (s, 3H); 2.12-2.18 (m, 2H); 4.38-4.45 (m, 1H); 6.75 (t, J=7.0, 1H).

Cyclopropylmethyl 2-(2-ethylcyclopropyl)acetate

Prepared from cyclopropylmethyl-3-hexenoate (70/30 Z/E mixture) according to the cyclopropanation method described above.

Bp.: 55° C./0.5 mbar $^{13}$C-NMR: 3.2 (t), 9.9 (d), 10.6 (t), 11.7 (d), 14.2 (q), 17.4 (d), 22.1 (t), 33.9 (t), 69.0 (t), 173.8 (s);

$^{1}$H-NMR: 0.26-0.30 (m, 2H); 0.54-0.58 (m, 2H); 0.69-0.83 (m, 2H); 0.98 (t, J=7.3, 3H); 1.07-1.41 (m, 5H); 2.16-2.41 (m, 2H); 3.93 (d, J=7.2, 2H).

(Z)-cyclobutylmethyl hex-3-enoate

Prepared from (Z) methyl hex-3-enoate and cyclobutanemethanol according to the ester preparation method B described above.

Bp.: 81° C./3 mbar $^{13}$C-NMR: 13.9 (q), 18.4 (t), 20.8 (t), 24.8 (t), 33.0 (t), 34.2 (d), 68.4 (t), 120.4 (d), 135.0 (d), 172.2 (s);

$^{1}$H-NMR: 0.98 (t, J=7.5, 3H); 1.72-2.10 (m, 8H); 2.56-2.67 (m, 1H); 3.08 (d, J=6.3, 2H); 4.06 (d, J=6.7, 2H); 5.49-5.60 (m, 2H).

Mixture of (Z)-cyclopropylmethyl 3-methylhept-2-enoate and (E)-cyclopropylmethyl 3-methylhept-2-enoate Prepared from ethyl 3-methyl-2-heptenoate and cyclopropyl methyl carbinol according to the ester preparation method B described above.

Purified by bulb to bulb distillation at 110° C./1 mbar

Major Isomer (E; 80%):

$^{13}$C NMR: 3.2 (t), 9.9 (d), 13.9 (q), 18.8 (q), 22.3 (t), 29.6 (t), 40.7 (t), 68.3 (t), 115.5 (d), 160.4 (s), 167.0 (s);

$^{1}$H-NMR: 0.26-0.30 (m, 2H); 0.54-0.58 (m, 2H); 0.91 (t, J=7.2, 3H); 1.10-1.18 (m, 1H); 1.29-1.36 (m, 2H); 1.43-1.50 (m, 2H); 2.14 (t, J=7.9, 2H); 2.16 (s, 3H); 3.92 (d, J=7.2, 2H); 5.7 (s, 1H).

Minor Isomer (Z; 18%):

$^{13}$C-NMR: 3.2 (t), 9.9 (d), 14.0 (q), 25.2 (t), 30.4 (t), 33.2 (t), 40.7 (t), 68.3 (t), 116.0 (d), 160.8 (s), 166.5 (s);

$^{1}$H-NMR: 0.26-0.30 (m, 2H); 0.54-0.58 (m, 2H); 0.92 (t, J=7.2, 3H); 1.10-1.18 (m, 1H); 1.29-1.36 (m, 2H); 1.43-1.50 (m, 2H); 1.88 (s, 3H); 2.63 (t, J=7.8, 2H); 2.16 (s, 3H); 3.91 (d, J=7.2, 2H); 5.7 (s, 1H).

(Z)-(1-methylcyclopropyl)methyl hex-3-enoate

Prepared from (Z) methyl hex-3-enoate and (1-methylcyclopropyl)methanol according to the ester preparation method B described above.

Purified by bulb to bulb distillation at 85° C./1 mbar $^{13}$C-NMR: 11.3 (t), 13.9 (q), 15.2 (s), 20.8 (t), 20.9 (q), 32.9 (t), 72.3 (t), 120.4 (d), 135.0 (d), 172.2 (s);

$^{1}$H-NMR: 0.35-0.37 (m, 2H); 0.46-0.49 (m, 2H); 0.99 (t, J=7.6, 3H); 1.12 (s, 3H); 2.04-2.11 (m, 2H); 3.11 (d, J=5.9, 2H); 3.89 (s, 2H); 5.50-5.62 (m, 2H).

Example 2

Preparation of a Perfuming Composition

A shower gel's perfuming composition, of the gourmand, fruity, musky type, was prepared by admixing the following ingredients:

| Ingredient | Parts by weight |
|---|---|
| Benzyl acetate | 350 |
| Anisic aldehyde | 290 |
| Hexylcinnamic aldehyde | 450 |
| 10%* Ethyl 2-methyl-pentanoate [1] | 50 |
| Gamma undecalactone | 150 |
| Allyl cyclohexylpropionate | 10 |
| Cis-2-pentyl-1-cyclopentanol [1] | 20 |
| (1'R,E)-2-ethyl-4-(2',2',3'-trimethyl-3'-cyclopenten-1'-yl)-2-buten-1-ol [1] | 50 |
| Ethylpraline | 35 |
| Ethylvanilline | 60 |
| 1,3-Benzodioxole-5-carbaldehyde [1] | 100 |
| Helvetolide ® [2] | 500 |
| Melonal ® [3] | 5 |
| Lilly of the valley composition [1] | 20 |
| Hedione ® [4] | 50 |
| Octanolide-1,4 | 270 |
| Orange essential oil | 100 |
| Hexyl salicylate | 380 |
| Vertofix Coeur ® [5] | 90 |
| | 2980 |

*in dipropyleneglycol
[1] origin: Firmenich SA, Geneva, Switzerland
[2] (1S,1'R)-2-[1-(3',3'-dimethyl-1'-cyclohexyl)ethoxy]-2-methylpropyl propanoate; origin: Firmenich SA, Geneva, Switzerland
[3] 2,6-dimethyl-5-heptanal; origin: Givaudan-Roure SA, Vernier, Switzerland
[4] methyl dihydrojasmonate; origin: Firmenich SA, Geneva, Switzerland
[5] methyl cedryl ketone; origin: International Flavors & Fragrances, USA The addition of 20 parts by weight of cyclopropylmethyl (3Z)-3-hexenoate to the above-described composition clearly imparted to the latter a fresh sparkling tonality reminding of a juicy green pear. This effect was not obtained with the addition of other derivatives of cis-3-hexenol which are known ingredients imparting green notes.

Example 3

Preparation of a Perfuming Composition

A perfuming composition, of the linden type, was prepared by admixing the following ingredients:

| Ingredient | Parts by weight |
|---|---|
| Benzyl acetate | 55 |
| Dodecyl acetate | 270 |
| Hydratropyl alcool | 205 |
| Anisic aldehyde | 20 |
| Cuminic aldehyde | 2 |
| Dihydro Eugenol | 20 |
| 1,3-Benzodioxole-5-carbaldehyde [1] | 15 |
| Hivernal ® [2] | 10 |
| Isoeugenol | 5 |
| Mayol ® [3] | 275 |
| Methylacetophenone | 5 |
| (1'R)-2-[2-(4'-methyl-3'-cyclohexen- | 3 |

-continued

| Ingredient | Parts by weight |
|---|---|
| 1'-yl)propyl] Cyclopentanone [1] | |
| 10%* Neobutenone ® Alpha [4] | 5 |
| Methyl Octin carbonate | 5 |
| 1%* Nonadienal | 5 |
| Phenethylol | 30 |
| Methyl salicylate | 5 |
| Terpineol | 20 |
| Undecavertol ® [5] | 5 |
| Ionone Alpha | 20 |
| 10%** Violettyne [6] | 15 |
| | 995 |

*in dipropyleneglycol
**in isopropyle myristate
[1] origin: Firmenich SA, Geneva, Switzerland
[2] 3-(3,3-dimethyl-5-indanyl)propanal; origin: Firmenich SA, Geneva, Switzerland
[3] cis-7-P-menthanol; origin: Firmenich SA, Geneva, Switzerland
[4] 1-(5,5-dimethyl-1-cyclohexen-1-yl)-4-penten-1-one; origin: Firmenich SA, Geneva, Switzerland
[5] 4-methyl-3-decen-5-ol; origin: Givaudan-Roure SA, Vernier, Switzerland
[6] 1,3-undecadien-5-yne; origin: Firmenich SA, Geneva, Switzerland The addition of 5 parts by weight of cyclopropylmethyl (3Z)-3-hexenoate to the above-described linden composition imparted to the latter a much more natural and sparkling connotation reinforcing the violet leaf aspects (provided by Methyl Octin carbonate, nonadienal, undecavertol and violettyne), as well as conferring a nice green, pear connotation.

When instead of the invention's compound there was added a derivatives of cis-3-hexenol, known to imparting green notes, the total effect was much less powerful and rising and also definitely devoid of the green, pear connotation.

What is claimed is:

1. A compound of formula

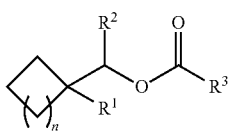

(I)

in the form of any one of its stereoisomers or of a mixture thereof, and wherein n is 0 or 1;
$R^1$ represents a hydrogen atom or a methyl or ethyl group;
$R^2$ represents a hydrogen atom or a methyl or ethyl group; and
$R^3$ represents:
a) a $C_5$-$C_8$ group of formula

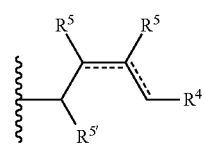

(i)

wherein one dotted line represents a carbon-carbon single or double bond and the other a carbon-carbon single bond;
$R^4$ represents a $C_{1-4}$ alkyl or alkenyl group;
$R^{5'}$ represents a hydrogen atom or a methyl group; and
each $R^5$, taken separately, represents a hydrogen atom or a methyl group, or two $R^5$, taken together, represent a $CH_2$ group (in such a case clearly both dotted lines represent a single bond); or $R^4$ and one $R^5$, taken together, represent a $C_{3-4}$ hydrocarbon group; or b) a $C_5$-$C_8$ group of formula

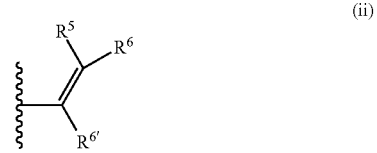

(ii)

wherein $R^6$ represents a $C_{3-4}$ alkyl or alkenyl group, $R^{6'}$ represents a hydrogen atom or a methyl or ethyl group, and $R^5$ is defined as above;

provided that cyclopropylmethyl 2,4-hexadienoate, cyclopropylmethyl hexanoate and cyclopropylmethyl octanoate are excluded.

2. The compound according to claim 1, wherein $R^{6'}$ represents a hydrogen atom.

3. The compound according to claim 1, wherein $R^3$ represents:

a$^i$) a $C_5$-$C_7$ group of formula

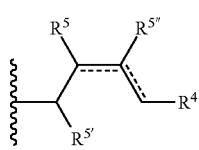

(i')

wherein one dotted line represents a carbon-carbon double bond and the other a carbon-carbon single bond;
$R^4$ represents a $C_{1-3}$ alkyl or alkenyl group, preferably alkyl;
$R^5$ and $R^{5'}$ represent each a hydrogen atom or a methyl group; and
$R^{5''}$, taken alone, represents a hydrogen atom or taken together with $R^5$ represents a $CH_2$ group (in such a case clearly both dotted lines represent a single bond);

a$^{ii}$) a $C_5$-$C_7$ group of formula

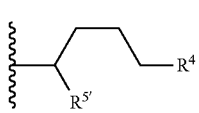

(i'')

$R^4$ represents a $C_{1-3}$ alkyl or alkenyl group, preferably alkyl;
$R^{5'}$ represents a hydrogen atom or a methyl group;

a$^{iii}$) a $C_6$-$C_8$ group of formula $CH_2(CH_2)_mR^7$, wherein m represents 0 or 1 and $R^7$ represents a $C_{5-6}$ cyclic alkyl or alkenyl group; or b') a $C_5$-$C_7$ group of formula

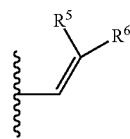

(ii')

wherein $R^5$ represents a hydrogen atom or a methyl group and $R^6$ represents a $C_3$ alkyl or alkenyl group.

4. The compound according to claim 1, wherein said compound is of formula

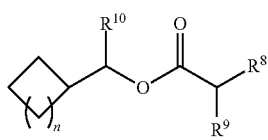

(II)

in the form of any one of its stereoisomers or of a mixture thereof, and wherein n is 0 or 1;
$R^{10}$ represents a hydrogen atom or a methyl group;
$R^8$ represents a hydrogen atom or a methyl group; and
$R^9$ represents a $C_{4-6}$ linear alkyl, alkenyl or alkadienyl group or a 2-$R^{11}$-cycloprop-1-yl group, $R^{11}$ representing a methyl, ethyl or propyl group.

5. A compound selected from the group consisting of cyclopropylmethyl (3Z)-3-hexenoate, (E)-cyclopropylmethyl hex-4-enoate or (Z)-cyclobutylmethyl hex-3-enoate, (E)-cyclopropylmethyl hex-2-enoate, cyclopropylmethyl 2-methylhexanoate, (Z)-1-cyclopropylethyl 3-hexenoate, cyclopropylmethyl 3-cyclohexylpropanoate, (E)-1-cyclopropylethyl 2-methylhex-2-enoate, cyclopropylmethyl (3E)-3-hexenoate, (Z)-cyclobutylmethyl hex-3-enoate, (Z)-cyclopropylmethyl 3-methylhept-2-enoate and (E)-cyclopropylmethyl 3-methylhept-2-enoate.

6. The compound according to claim 5, which is cyclopropylmethyl (3Z)-3-hexenoate, or (E)-cyclopropylmethyl hex-4-enoate or (Z)-cyclobutylmethyl hex-3-enoate.

7. A method to confer, enhance, improve or modify the odor properties of a perfuming composition or of a perfumed article, which method comprises adding to said composition or article an effective amount of at least a compound of formula

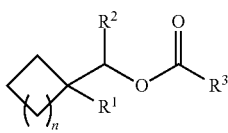

(I)

in the form of any one of its stereoisomers or of a mixture thereof, and wherein n is 0 or 1;
$R^1$ represents a hydrogen atom or a methyl or ethyl group;
$R^2$ represents a hydrogen atom or a methyl or ethyl group; and
$R^3$ represents:
a) a $C_5$-$C_8$ group of formula

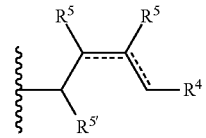

(i)

wherein one dotted line represents a carbon-carbon single or double bond and the other a carbon-carbon single bond;

$R^4$ represents a $C_{1-4}$ alkyl or alkenyl group;
$R^{5'}$ represents a hydrogen atom or a methyl group; and each $R^5$, taken separately, represents a hydrogen atom or a methyl group, or two $R^5$, taken together, represent a $CH_2$ group (in such a case clearly both dotted lines represent a single bond); or $R^4$ and one $R^5$, taken together, represent a $C_{3-4}$ hydrocarbon group; or
b) a $C_5$-$C_8$ group of formula

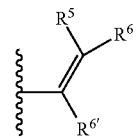

(ii)

wherein $R^6$ represents a $C_{3-4}$ alkyl or alkenyl group, $R^{6'}$ represents a hydrogen atom or a methyl or ethyl group, and $R^5$ is defined as above.

8. The method according to claim 7, wherein said compound is cyclopropylmethyl (3Z)-3-hexenoate, (E)-cyclopropylmethyl hex-4-enoate or (Z)-cyclobutylmethyl hex-3-enoate, (E)-cyclopropylmethyl hex-2-enoate, cyclopropylmethyl 2-methylhexanoate, (Z)-1-cyclopropylethyl 3-hexenoate, cyclopropylmethyl 3-cyclohexylpropanoate, (E)-1-cyclopropylethyl 2-methylhex-2-enoate, cyclopropylmethyl (3E)-3-hexenoate, (Z)-cyclobutylmethyl hex-3-enoate, (Z)-(1-methylcyclopropyl)methyl hex-3-enoate, (Z)-cyclopropylmethyl 3-methylhept-2-enoate or (E)-cyclopropylmethyl 3-methylhept-2-enoate.

9. The method according to claim 7, which is cyclopropylmethyl (3Z)-3-hexenoate, or (E)-cyclopropylmethyl hex-4-enoate or (Z)-cyclobutylmethyl hex-3-enoate.

10. A perfuming ingredient in the form of a composition comprising
i) at least one compound of formula (I), as defined in claim 1;
ii) at least one ingredient selected from the group consisting of a perfumery carrier and a perfumery base; and
iii) optionally at least one perfumery adjuvant.

11. The perfuming ingredient according to claim 10, wherein the compound is selected from the group consisting of cyclopropylmethyl (3Z)-3-hexenoate, (E)-cyclopropylmethyl hex-4-enoate or (Z)-cyclobutylmethyl hex-3-enoate, (E)-cyclopropylmethyl hex-2-enoate, cyclopropylmethyl 2-methylhexanoate, (Z)-1-cyclopropylethyl 3-hexenoate, cyclopropylmethyl 3-cyclohexylpropanoate, (E)-1-cyclopropylethyl 2-methylhex-2-enoate, cyclopropylmethyl (3E)-3-hexenoate, (Z)-cyclobutylmethyl hex-3-enoate, (Z)-cyclopropylmethyl 3-methylhept-2-enoate and (E)-cyclopropylmethyl 3-methylhept-2-enoate.

12. The perfuming ingredient according to claim 10, which is cyclopropylmethyl (3Z)-3-hexenoate, or (E)-cyclopropylmethyl hex-4-enoate or (Z)-cyclobutylmethyl hex-3-enoate.

13. A perfuming consumer product:
i) as perfuming ingredient, at least one compound of formula (I), as defined in claim 1; and
ii) a perfumery consumer base.

14. The consumer product according to claim 13, wherein the compound is selected from the group consisting of cyclopropylmethyl (3Z)-3-hexenoate, (E)-cyclopropylmethyl hex-4-enoate or (Z)-cyclobutylmethyl hex-3-enoate, (E)-cyclopropylmethyl hex-2-enoate, cyclopropylmethyl 2-methylhexanoate, (Z)-1-cyclopropylethyl 3-hexenoate, cyclopropylmethyl 3-cyclohexylpropanoate, (E)-1-cyclopropylethyl 2-methylhex-2-enoate, cyclopropylmethyl (3E)-3-hexenoate, (Z)-cyclobutylmethyl hex-3-enoate, (Z)-cyclopropylmethyl 3-methylhept-2-enoate and (E)-cyclopropylmethyl 3-methylhept-2-enoate.

15. The consumer product according to claim 13, which is cyclopropylmethyl (3Z)-3-hexenoate, or (E)-cyclopropylmethyl hex-4-enoate or (Z)-cyclobutylmethyl hex-3-enoate.

16. The consumer product according to claim 13, wherein the perfumery consumer base is a perfume, a fabric care product, a body-care product, an air care product or a home care product.

17. The consumer product according to claim 13, wherein the perfumery consumer base is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *